United States Patent [19]
Peterson

[11] Patent Number: 6,129,693
[45] Date of Patent: Oct. 10, 2000

[54] BLADDER SEAT FOR USE WITH TRACTION DEVICE

[76] Inventor: Gregory K. Peterson, 21 N. Oaks Rd., St. Paul, Minn. 55127

[21] Appl. No.: 09/022,689

[22] Filed: Feb. 12, 1998

[51] Int. Cl.[7] ............................... A61F 5/00; A61H 1/02
[52] U.S. Cl. ........................... 602/32; 606/241; 297/338; 297/452.41
[58] Field of Search ..................... 606/241, 242; 602/13, 32–36, 38–40; 601/24; 128/845; 5/81.1 R, 648, 654, 655.3, 655.9, 709; 297/338, 344.12, 344.19, 452.41; 482/143

[56] References Cited

U.S. PATENT DOCUMENTS

| | | | |
|---|---|---|---|
| 3,276,047 | 10/1966 | Emery | 5/654 |
| 4,113,220 | 9/1978 | Godwin et al. | 297/344.19 |
| 4,371,997 | 2/1983 | Mattson | 5/654 |
| 4,422,452 | 12/1983 | Burton . | |
| 4,569,340 | 2/1986 | Burton . | |
| 4,981,307 | 1/1991 | Walsh | 5/81.1 R |
| 5,033,133 | 7/1991 | Nissen | 5/709 |
| 5,088,476 | 2/1992 | Burton | 606/241 |
| 5,195,949 | 3/1993 | Burton et al. . | |
| 5,303,435 | 4/1994 | Haar et al. . | |
| 5,487,197 | 1/1996 | Iskra, Jr. et al. | 5/654 |

OTHER PUBLICATIONS

That Aching Back!; Jul. 14, 1980 issue of Time magazine; By Anastasia Toufexis; pp. 30–38.
Bare–Bone Facts About Your Aching Back; Condensed from Time; Anastasia Toufexis; pp. 97–100.
The Biomechanics of Gravity—Dependent Traction of the Lumbar Spine; Janke, Kerkow, Griffiths, Sparrow & Iaizzo; Sep. 22, 1995; pp. 1–36.

*Primary Examiner*—John Mulcahy
*Assistant Examiner*—Victor Hwang
*Attorney, Agent, or Firm*—Merchant & Gould P.C.

[57] ABSTRACT

A seat 100 is used with a device 10 for transferring stress from the lumbar spine to the rib cage of a person. The device 10 includes torso embracing members 29 and 30 and a seat 100 supported by the device 10. The seat includes a fluid tight chamber 106 and a fluid control device for controlling flow of fluid into and out of the chamber 106. The chamber has a first height when filled with fluid and a second, lesser height when fluid has been removed from the chamber.

23 Claims, 4 Drawing Sheets

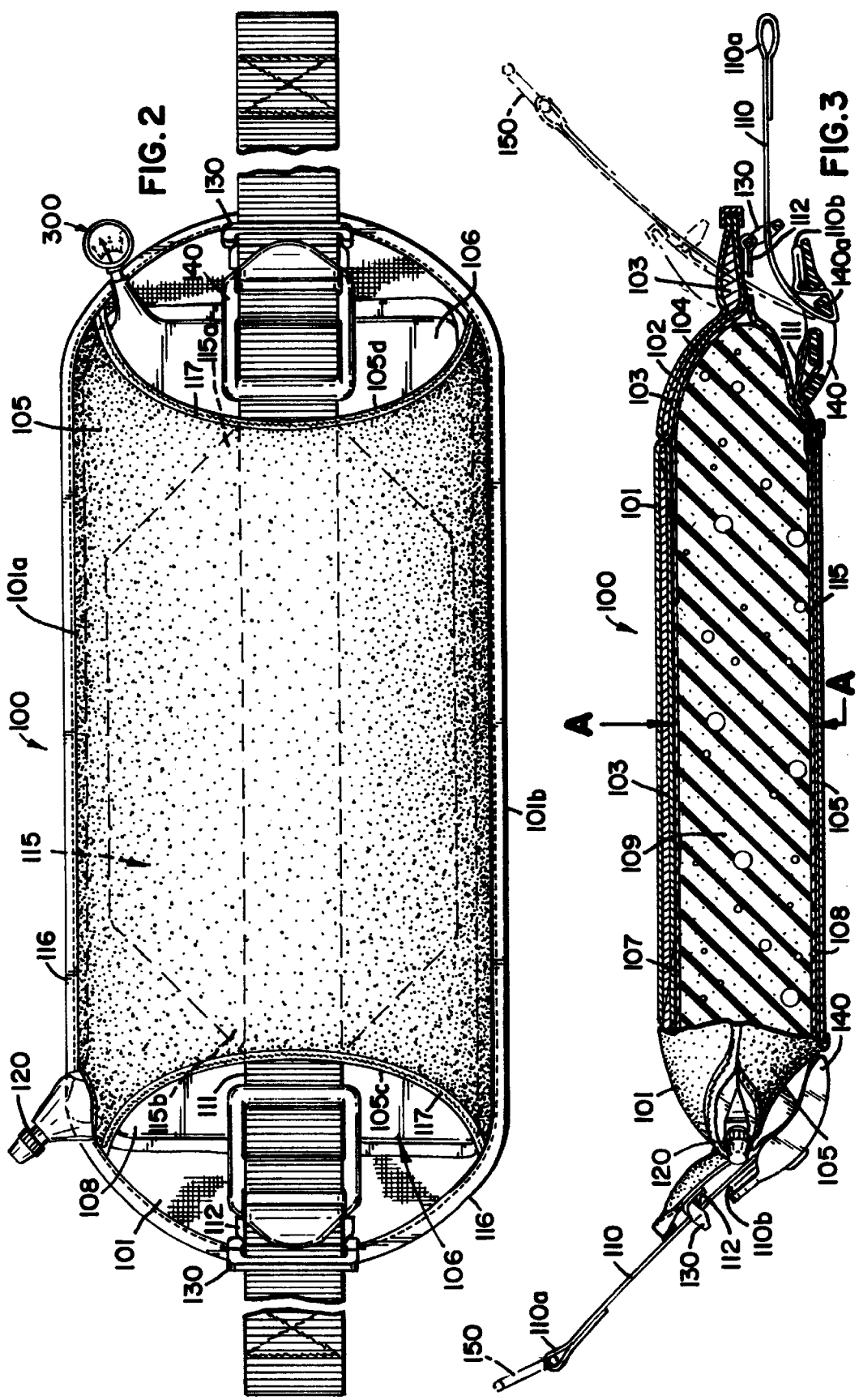

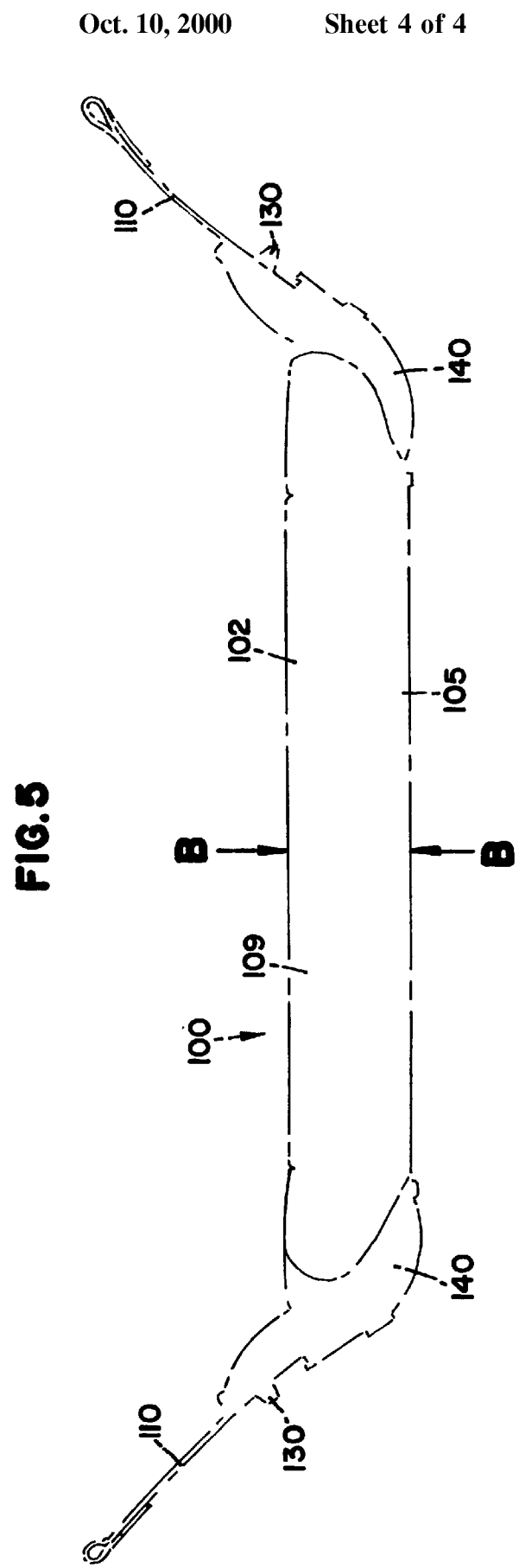

BLADDER SEAT FOR USE WITH TRACTION DEVICE

BACKGROUND OF THE INVENTION

1. Field of the Invention

This invention refers generally to an apparatus for transferring weight stress and loading from the lumbar spine to a rib cage of an individual to obtain benefits associated with unloading the spine. More specifically, this invention relates to a fluid filled bladder for use as a seat whereby the amount of stress transferred may be adjusted by adding or removing fluid from the bladder.

2. Description of the Prior Art

Back pain is a common and significant malady afflicting large numbers of people and virtually every country of the world. The wide spread nature of the problem has been highlighted in numerous articles printed in both medical and new periodicals. Illustrative are articles entitled Bare-bones Facts About Your Aching Back from the December, 1980 issue of *Readers Digest* and the cover story from Jul. 14, 1980 issue of *Time* magazine.

Axial traction has been shown to be effective in treating certain types of low back ailments, in preventing back ailments and in producing and sustaining low back health. Such traction has been found to be an effective means of realigning improperly aligned or displaced vertebral elements as well as their associated invertebral discs and soft tissues. Such traction when used periodically for sustained periods has also been shown to reduce herniated contained intervertebral discs. Further, such traction has also been shown (in muscle and ligament injury or insult) to reduce spasm and inflammation, enhance blood flow and to promote optimal healing. Certain circumstances have, however, long presented obstacles to the effective application of controlled traction to the lumbar area. These circumstances include the significant amount of force which must be applied, the lack of a location at which the axially directed force can be applied, and the position of the person during which the axial force is being applied.

In 1971, Charles Burton, M.D. provided for the construction of an apparatus to support a person, such person having one of a number of conditions such as a protruded lumbar disc, in a vertical position wherein the torso of the person was suspended from above by a chest harness and vest encircling the rib cage. As a result of related research and experience it has been demonstrated scientifically and conclusively that the rib cage can serve as an optimum site of fixation and does serve well this purpose. In order for the overhead harness vest to function most effectively, it was observed that it should, at its lower end, be tightened beneath the rib cage so that, as axial force is applied by the body's weight to the harness, the rib cage will not slide out of the harness of vest.

After continued research, an improved gravity traction vest was developed. Prior to this time, the tightening of a lower most belt of the gravity vest was accomplished exclusively by providing a belt having a sufficient number of locking points whereby the belt could be tightened so that it was within the perimeter of the rib cage regardless of the size of the person being treated. The new improved gravity traction vest (shown in U.S. Pat. No. 4,422,452) provided means whereby axial fixation could be efficiently accomplished, yet wherein the treatment is not rendered uncomfortable.

While the improved second generation gravity traction vest provided improvement over the original gravity traction vest, there remained a number of problems associated with its use. Their problems included the need to tighten a number of cinctures to secure the vest to the person, the rough surfaces of the cinctures being felt through the vest by the person. While there was an improved locking of the vest to the person due to a cushion insert, it was desirable to provide for still more positive locking. The need to provide improved comfort to the persons has always been a goal which each new generation of product has tried to accomplish. The goal was to provide a vest which allowed the person to experience gravity traction without causing unnecessary discomfort. While there has been improvement in this area, there has been the need for still more improvement.

It is these problems in the prior art that a third generation gravity traction vest was developed. It provides for a torso surrounding member being constructed of a rigid material, a simple and effective means for securing the vest to the person and a flanged under portion that protrudes inwardly toward the person for engagement below both the lowest rib and the inverted U-shaped area of the rib cage. U.S. Pat. No. 4,569,340 was issued on Feb. 11, 1986 on such a vest.

While such vests have been utilized for many persons and have proved quite successful, all of the vests to date have required overhead support of the vest. This is a drawback in that such devices are large and cumbersome and are best utilized in a hospital or clinic setting.

U.S. Pat. No. 5,195,949 discloses a traction seating device which includes a pair of pivotal arm assemblies on which are mounted torso embracing members. Beneath the torso engaging members is a seat. The person using the traction seating device is able to transfer weight from the seat to the torso embracing members by lowering the seat.

However, to date there has sometimes been problems with adjusting the seat while the person is utilizing the device. It is sometimes difficult for the adjustable strap, which is attached to the seat, to be lowered in a controlled manner. The seat and strap should allow for a smooth reduction of weight bearing on the strap to allow for further unloading. This can either be done uniformly (both sides simultaneously) or differentially (with side-to-side variation).

A person can become adept at lowering the strap of the prior art design and control the actions smoothly. The seat typically starts out at a higher level when the person enters the axial unloading device and then it is gradually lowered to allow for more unloading. After each loading session, it is necessary that the strap be adjusted back to the starting position. The starting position is normally the same for the beginning of each unloading session. For certain persons, specifically those with reduced hand and finger strength, low coordination skills and/or oversize or large hips all of which can impede the proper lowering of the strap, the prior art device may be very difficult to use. These physical constraints may render the traction device unusable, because the person cannot effectively reduce the weight on the strap.

Accordingly, the present invention addresses this problem associated with the prior art and provides for a seat member whose height may be easily adjusted while the traction device is in use.

SUMMARY OF THE INVENTION

The present invention is a seat for use with a device for transferring stress from a lumbar spine to the rib cage of the person. The device has a torso embracing member and the seat is operatively connected to the device for at least partially supporting the person. The seat include a fluid tight chamber and a fluid control device for controlling the flow of fluid into and out of the chamber. The chamber has a first height when filled with fluid and a second, lesser height when fluid has been removed from the chamber.

The present invention is also a seat for use with a device for transferring stress from a lumbar spine to a rib cage of a person. The device has a torso embracing member and a seat operatively connected to the device for at least partially supporting the person. The seat comprises a self-inflating air chamber and a valve operatively connected to the chamber for controlling flow of air into and out of the chamber. A cover, having a first and second ends, carries the chamber. A first strap is operatively connected to the first end of the cover and a second strap is operatively connected to the second end of the cover. The second ends of the strap are for being operatively connected to the device. The chamber has a first height when filled with air and a second, lesser height when air has been removed from the chamber.

The invention is also a device for transferring stress from a lumbar spine to a rib cage of a person. The device includes a torso engaging member for at least partially surrounding the torso and for supporting a person proximate a person's waist below the rib cage. A structure is configured to support the torso engaging member and a seat is operatively connected to the device. The seat includes a fluid tight chamber and a fluid control device for controlling flow of fluid into and out of the chamber. The chamber has a first height when filled with fluid and a second, lesser height when fluid has been removed from the chamber, wherein the torso embracing member supports the person and stress is transferred from the lumbar spine to the rib cage and stress transferred may be increased by removing fluid from the chamber.

The invention is also a method of adjusting the amount of stress transferred from a lumbar spine to a rib cage of a person while using a traction device having a torso engaging member. The device includes a support structure for supporting the torso engaging member and a seat operatively connected to the device. The seat has a fluid tight chamber. The method includes engaging the torso engaging member about a person's rib cage while the fluid chamber is at a first, filled, height. Then, fluid is moved out of the fluid chamber so that the chamber is at a second, at least partially evacuated height, wherein more stress is transferred due to the lower end of the fluid chamber's height.

BRIEF DESCRIPTION OF THE DRAWINGS

FIG. 2 is a bottom plan view of the seat showing in FIG. 1;

FIG. 3 is a cross-sectional view taken generally along the lines 3—3 of FIG. 1, in an inflated condition;

FIG. 5 is a schematic representation of the seat shown in FIG. 3, in a deflated condition.

DETAILED DESCRIPTION OF THE PREFERRED EMBODIMENT

Figure 1:
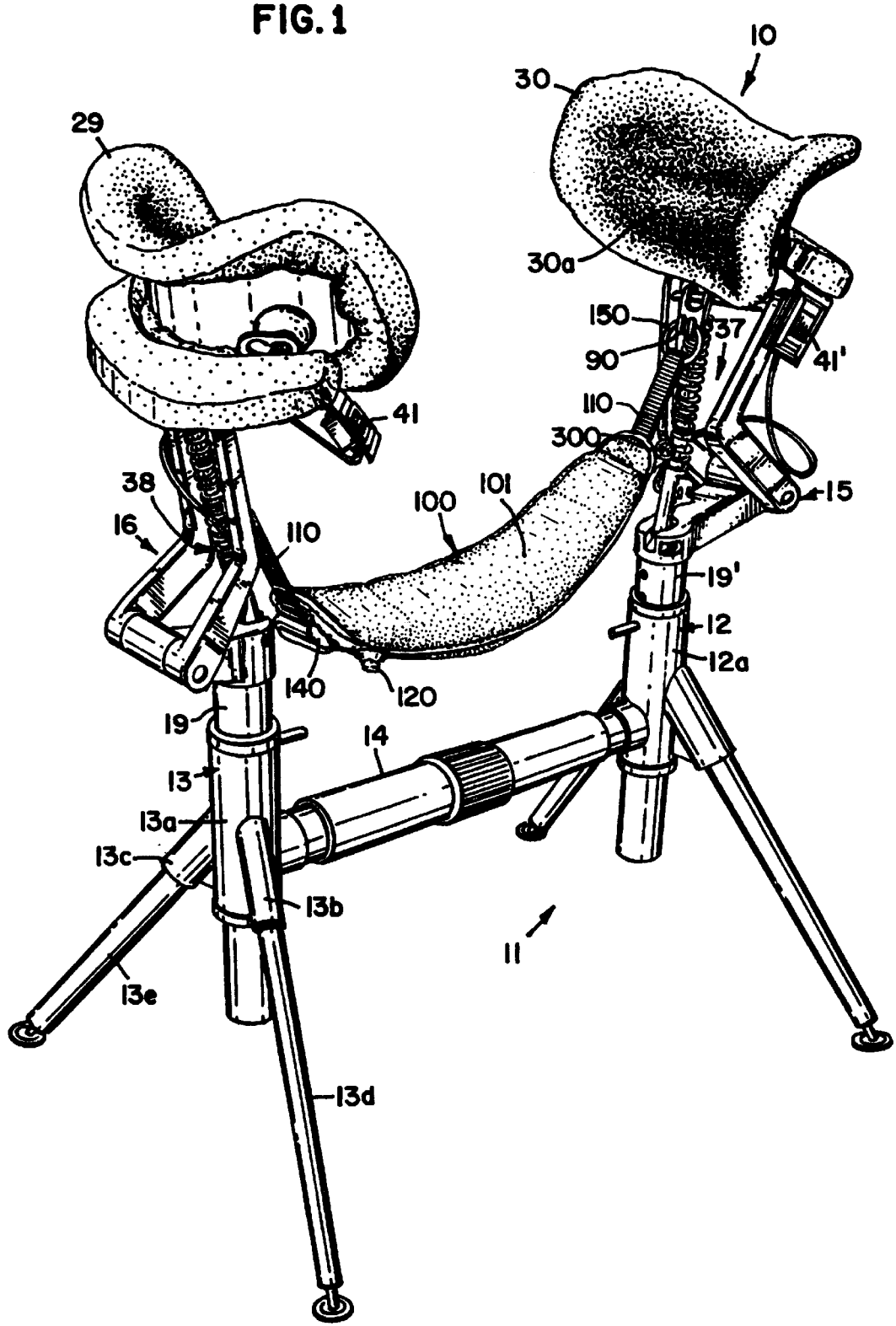
FIG. 1 is a perspective view showing one embodiment of the present invention.

Referring to the drawing, wherein like numerals represent like parts throughout several views, there is generally disclosed at 10 a traction seating device. Except for the seat and strap assembly (to be described more fully hereafter) the traction device 10 is similar to that shown in U.S. Pat. No. 5,195,949 which is hereby incorporated by reference. The traction device 10 will be described with respect to it's major components. As U.S. Pat. No. 5,195,949 has been incorporated by reference, further specific details may be seen in that patent. The device 10 includes a base support generally designated at 11. The base support includes a first upright member 12 and a second upright member 13. The uprights 12 and 13 are mirror images of each other. The upright 13 has two generally outward and downwardly depending legs supports 13b and 13c which are configured to receive legs 13d and 13 e. A connector 14 is utilized to connect the two legs 12 and 13. The connector 14 may have components that are threadably engaged to increase or decrease the distance as shown in the drawing. Alternately, they may be simply telescoping components which are appropriately secured in place by a suitable fastener.

The first pivot arm 15 is operatively connected to the first upright member 12 and a second pivot arm assembly generally designated as 16 is operatively connected to the second upright member 13. The pivot arm 16 is operatively connected to cylindrical extension member 19 for movement in the cylinder 13a of cylinder 13.

The pivot arm 15 is operatively connected to a cylinder extension 19' for movement in the cylinder 12a of cylinder 12.

Two arcuate torso embracing members 29 and 30 are utilized. The members 29 and 30 are mirror images of each other. The member 29 is arcuate in shape and is shaped and configured to engage the person utilizing the device approximately at the waistline and a protrusion 30a is formed approximately in the center of member 30. The protrusion 30a is designed to fit immediately under the rib cage and ultimately provide support under the rib cage of the person utilizing the device 10. Linear locks 37 and 38 are spring clutch devices which are controlled by switches 41 and 41' to allow the locking device to be locked in a plurality of positions as the torso embracing members 29 and 30 are pivoted about the pivot arm. An L-shaped hook 90 is attached to the pivot arm 15 under the torso embracing member 30. As will be described more fully hereafter, the L-shaped clip 90 is adapted to having a D ring 150 slip over the top of the L-shaped hook 90 and is used to secure a seat to the device 10. A similar L-shaped hook is attached to the arm 16.

The seat, generally designated as 100, is shown in more detail in FIGS. 2, 3, and 5. Seat 100 includes a fluid tight chamber 106 that is carried in a cover 102. A strap assembly is connected to the cover and connects the seat 100 to the traction device 10.

The cover 102 may be constructed from many materials that can be fabricated into a shell. This could either be done by way of sewing fabric together, as shown in the figures, by gluing or bonding or by other suitable methods such as injection molding to form a cover for the fluid tight chamber 106. The cover includes a top sheet 101 which is operatively connected to the bottom sheet 105 by suitable means such as stitching. A reinforcing strip 116 is sewn around the outer periphery of the top sheet 101 and the bottom sheet 105 is also stitched to the reinforcing strip 116 along its sides 101a and 101b. The sides 105c and 105d have a reinforcing strip 117 attached thereto. However, the sides 105c and 105d are not attached to the top sheet 101. Therefore, an inner cavity is formed in which the bladder 106 may be positioned. A pad 103 is positioned between the top sheet 101 and a bottom layer 104. The pad 103 is for additional comfort for the person sitting on the seat 100. The pad 103 is less important in the central region of the seat. However, in the outer portions of the seat 100, the pad 103 provides extra protection and padding for the person when seated on the seat 100 and the straps 110 are upright. In fact, in viewing FIG. 3, it can be seen that the pad 103 is thicker proximate the clamp 140.

The fluid tight chamber 106 includes a top bladder wall 107 operatively connected to a bottom bladder wall 108 to define a fluid tight chamber. An open cell-urethane foam 109 may be positioned inside of the fluid tight chamber 106. A valve 120 is operatively connected to the fluid tight chamber 106 to allow any fluid within the chamber 106 to be expelled or admitted. One advantage of using the open celled foam 109 is that the fluid tight chamber then becomes self-inflating with air. The use of such a construction is well known in the camping industry such as that shown in U.S. Pat. No. 5,303,435. Straps 110 are operatively connected to the cover 102. The straps 110, loop 130 and clamp 140 are similar on both sides of the cover 102. The loop 130 has an attachment strap 112 operatively connected to the under side of the bottom layer 104. The attachment strap 112 forms a loop to include one side of the loop 130. The clamp 140 has a clamp attachment strap 111 which is operatively connected to the inside of the bottom sheet 105. The strap 110 has a loop formed at its first end 110a and a second end 110b which has passed through the loop 130 and around the clamping member 140a of clamp 140. This allows the length of the strap 110 to be adjusted by simply pulling the end 110b further through the clamping member 140a of clamp 140. Such adjustable clamp and loop assemblies are well known in the art. The loop at end 110a is adapted to receive the D-ring 150 which is in turn used to secure the seat 100 to the device 10.

Since a large force is applied to the clamp attachment strap 111, the straps 111 are sewn not only to the bottom sheet 105 but also to a web structure 115. The web structure 115 is of a flexible nature but still resistant to stretching while under tension. The web 115 has its two ends 115a and 115b sewn to the bottom sheet 105 at the same position that the straps 111 are secured to the bottom sheet.

The valve 120 is positioned so that it extends beyond the front edge of the seat 100. An opening in the connection between the top sheet 101 and bottom sheet 105 provides a small opening for the valve to extend through. An extension may be provided for the valve 120, such that it would extend to a position proximate the switch 41 to allow for easier operations by a large or heavier person.

While the fluid tight chamber has been described as having an open celled foam that is self-inflating, it is understood that other fluid tight chambers may be used. For instance, the chamber may use simply air or water. If the chamber is not self-inflating, it would then be necessary to add air back into the chamber, by some suitable means, when it is desired to refill the chamber. If the fluid was water, it would be necessary to provide a means to capture the water coming out of the chamber and later be able to reinsert it into the chamber when it was desired to go back to the original height. A gauge 300 may be incorporated to measure pressure within the chamber indicating the amount of fluid remaining which can be correlated to a change in chamber height. The gauge may be any suitable gauge and would be connected to the fluid tight chamber similar to the valve 120. While not shown, an opening may be provided between the sheets 101 and 105, as is done for the valve 120, and the gauge may be positioned with a suitable extension tube so as to be viewable by the seat or device user. The valve 120a and the gauge 300 may also be cooperatively connected in line with one another.

FIG. 3 shows the seat in a first, or fully inflated/expanded condition. In this condition, the seat 10 is at its greatest height. The height of the bladder 106 is shown as the distance between arrows A—A in FIG. 3. FIG. 5 shows the condition of the bladder 106 and therefore the seat 100 after the fluid has been released from the fluid tight chamber 106. The height, designated between arrows B—B is less than the height A—A. The height can be easily adjusted to any position between full height and the minimum height by simply opening the valve 120 until all of the fluid is displaced.

Figure 4:
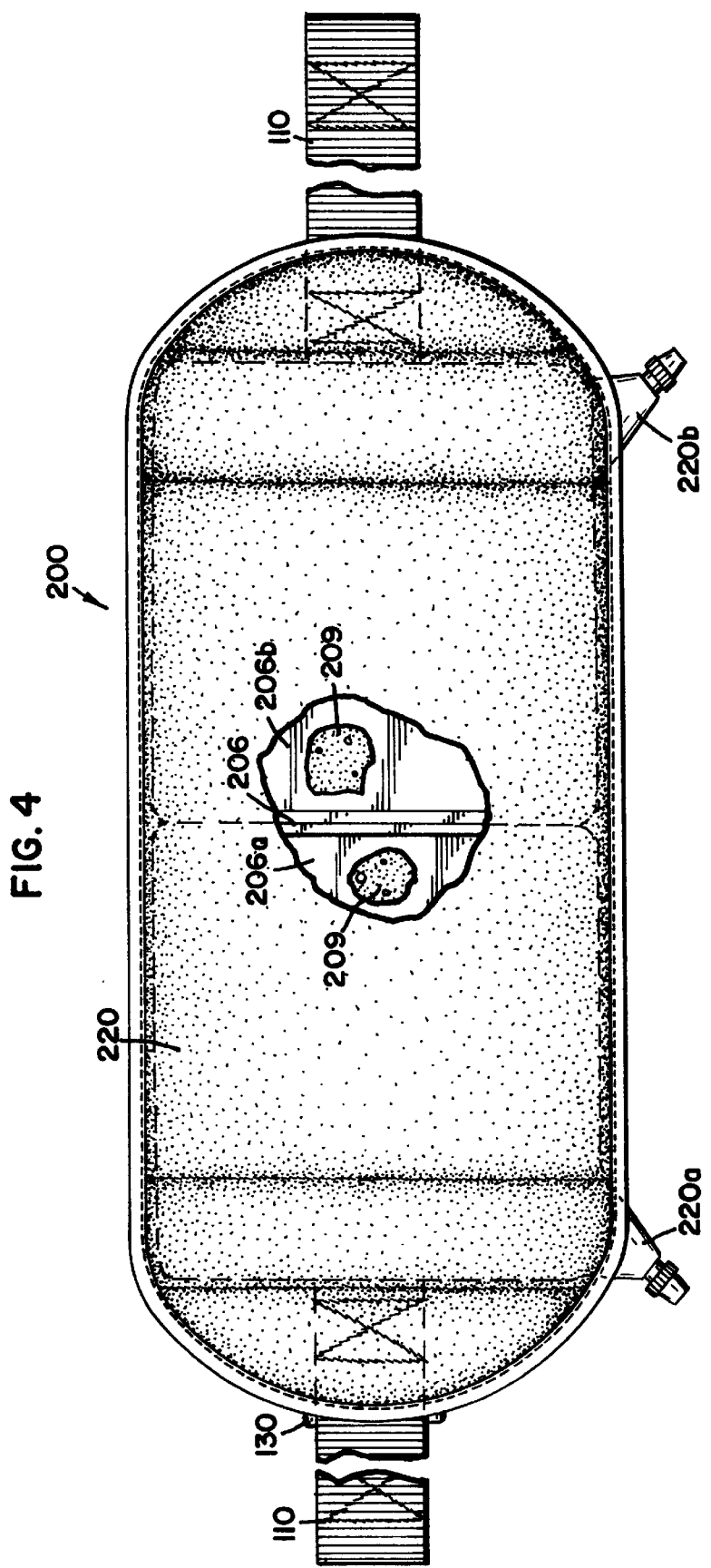
FIG. 4 is a top plan view of a second embodiment of a bladder for use with the present invention.

FIG. 4 represents another embodiment of the seat and is generally designated 200. The seat 200 is similar to the seat 100 with the exception that a different fluid type chamber is utilized. The seat 200 utilizes the same straps 110, clamps 140, and loops 130. Similarly, the construction of the cover 220 is similar to that of the cover 102 with the exception that there are two openings for the valves 220a and 220b which will be discussed more fully hereinafter. The fluid tight chamber 206 includes a first fluid tight chamber 206a and a second fluid tight chamber 206b. Each chamber 206a and 206b are similar to chamber 106 with the exception of their size. The fluid tight chamber 206a has a valve 220a associated therewith and the fluid tight chamber 206b has a valve 220b fluidly connected thereto. Open celled foam 209 is used in each chamber. The chambers 206a and 206b are not in fluid communication with each other and operate independently through their respective valves 220a and 220b. Gauges can be employed to inform the seat or device user regarding the pressure in each chamber, 206a and 206b.

In operation, the straps 110 are adjusted to the initially desired setting. Then the person enters the traction device 10 and sits on the seat 100 thereby causing the torso engaging members 29 and 30 proximate the ribcage of the person using the device to support the person. When doing this, the chamber 106 is typically in a filled or at a height which is at its maximum height. Then, the person using the device 10 opens the valve 120 and allows for air to be forced out of the fluid tight chamber 106. This then permits the chamber to go to a second height which is less than the first height. Since the person using the device 10 is held stationary about the ribcage, this provides for less weight to be supported by the seat and therefore more weight to be supported by the torso engaging members 29 and 30, thereby increasing the amount of axial unloading. The contents of the fluid tight chamber may be released in whole or in part dependent upon the needs of the person. The valve can be closed at the desired amount of weight reduction on the strap and any remaining portion of the fluid is held within the chamber. The reduction in weight bearing on the seat strap reduces the weight bearing on the physical structure of the person's low back.

Upon completion of the use of the device 10, the person gets out of the device 10. In the case of a self-inflating chamber, the valve 120 is opened and the pillow refills. Upon refilling, the valve 120 can be closed and the device 10 is ready for use by the next person. If, in other embodiments, the chamber is not self-inflating, it would be necessary to refill the chamber by a suitable means.

In the embodiment described with respect to FIG. 4, it is possible to release valves 220a and 220b so that the release is uniform from side to side or there may be side to side differences as may be desired and necessary for persons having certain conditions.

The above specification, examples and data provide a complete description of the manufacture and use of the composition of the invention. Since many embodiments of the invention can be made without departing from the spirit and scope of the invention, the invention resides in the claims hereinafter appended.

I claim:

1. A seat for use with a device for transferring stress from a lumbar spine to the rib cage of a person, the device having a torso embracing member, the seat operatively connected to the device for at least partially supporting the person, the seat comprising:

a cushion comprising:
 (a) an enclosure in a fluid tight chamber;
 (b) a fluid control device for controlling flow of fluid into and out of the chamber;
 (c) the chamber having a first height when filled with fluid and a second, lesser height when fluid has been removed from the chamber; and
a support assembly connected to the seat for operatively suspending said cushion, said seat and a person seated thereon from the device;
wherein stress is transferred from the lumbar spine to the rib cage by removing fluid from the chamber.

2. The seat of claim 1, wherein the fluid is air.

3. The seat of claim 2, wherein the chamber is self-inflating.

4. The seat of claim 3, wherein the chamber is constructed from an open cell foam and the control device is a valve.

5. The seat of claim 1, further comprising a cover for the chamber, the cover comprising:
a top member, having first and second ends, operatively connected to a bottom member, having first and second ends, wherein a cavity is formed between the members, the chamber positioned in the cavity.

6. The seat of claim 5, wherein the support assembly comprises a first strap having a first end operatively connected to the first end of the bottom member and a second strap having a first end operatively connected to the second end of the bottom member, the second ends of the strap for connecting to the device, wherein the top member is positioned between the straps and the person to protect the person.

7. The seat of claim 5, further comprising the control device extending away from the chamber and proximate the seat's front edge for easy access by the person.

8. The seat of claim 1, wherein the control device is a valve.

9. The seat of claim 1, wherein the chamber comprises a first sub-chamber and a second sub-chamber, and each sub-chamber having a control device for independently controlling flow of fluid from each sub-chamber.

10. The seat of claim 1, further comprising a gauge in fluid communication with the fluid tight chamber, wherein pressure may be monitored and correlated to a height of the chamber.

11. A seat for use with a device for transferring stress from a lumbar spine to a rib cage of a person, the device having a torso embracing member, the seat operatively connected to the device for at least partially supporting the person, the seat comprising:

(a) a seat cushion comprising:
 (i) an enclosure with a self-inflating air chamber;
 (ii) a control device operatively connected to the chamber for controlling flow of air into and out of the chamber;
 (iii) a cover, having first and second ends, in which the chamber is placed;

(b) a strap assembly comprising:
 (i) a first strap having a first end operatively connected to the first end of the cover and a second strap having a first end operatively connected to the second end of the cover;
 (ii) the second ends of the strap for operatively suspending the cushion and seat from the device; and
(c) the chamber having a first height when filled with air and a second, lesser height when air has been removed from the chamber, wherein stress is transferred from the lumbar spine to the rib cage by removing fluid from the chamber.

12. The seat of claim 11, wherein the chamber is constructed from an open cell foam and the control device is a valve.

13. A device for transferring stress from a lumbar spine to a rib cage of a person, the device comprising:
(a) a torso engaging member for at least partially surrounding the torso and for supporting a person proximate a person's waist below the rib cage;
(b) a structure configured to support the torso engaging member;
(c) a seat operatively suspended from the device, the seat having a seat cushion comprising:
 (i) a fluid tight chamber;
 (ii) a fluid control device for controlling flow of fluid into and out of the chamber; and
 (iii) the chamber having a first height, when filled with fluid and a second, lesser height when fluid has been removed from the chamber, wherein the torso embracing member support the person and stress is transferred from the lumbar spine to the rib cage and the stress transferred may be increased by removing fluid from the chamber.

14. The device of claim 13, wherein the fluid is air.

15. The device of claim 14, wherein the chamber is self-inflating.

16. The device of claim 15, wherein the chamber is constructed from open cell foam and the control device is a valve.

17. The device of claim 16, further comprising a cover for the chamber, the cover comprising:
a top member, having first and second ends, operatively connected to a bottom member, having first and second ends, wherein a cavity is formed between the members, the chamber positioned in the cavity.

18. The device of claim 17, further comprising a first strap having a first end operatively connected to the first end of the bottom member and a second strap having a first end operatively connected to the second end of the bottom member, the second ends of the straps for connecting to the device, wherein the top member is positioned between the straps and the person to protect the person.

19. The device of claim 18, further comprising the control device extending away from the chamber and proximate the seat's front edge for easy access by the person.

20. A method of adjusting the amount of stress transferred from a lumbar spine to a rib cage of a person while using a traction device having a torso engaging member, a structure to support the torso engaging member and a seat operatively connected to the device, the seat having a seat cushion comprising a fluid tight chamber and a control device for controlling flow of fluid into and out of the chamber, comprising;

(a) engaging the torso engaging member about a person's rib cage while the fluid chamber is at a first, filled height; and (b) moving fluid out of the fluid chamber so that the chamber is at a second, at least partially evacuated, height;

(c) wherein more stress is transferred due to lowering of the fluid chamber's height.

21. A seat for use with a device for transferring stress from a lumbar spine to the rib cage of a person, the device having a torso embracing member, the seat operatively connected to the device for at least partially supporting the person, the seat comprising:

(a) a fluid tight chamber;

(b) a fluid control device for controlling flow of fluid into and out of the chamber; the chamber having a first height when filled with fluid and a second, lesser height when fluid has been removed from the chamber;

(c) a cover for the chamber, comprising a top member having first and second ends, a bottom member having first and second ends and operatively connected to said top member, wherein a cavity is formed between said top and bottom members and said chamber is positioned in said cavity; and (d) a first strap having first and second ends, said first end thereof operatively connected to the first end of the bottom member and a second strap having first and second ends, said first end thereof operatively connected to the second end of the bottom member, the second ends of the first and second straps for connecting to the device; wherein the top member is positioned between the first and second straps and the person, to protect the person.

22. A device for transferring stress from a lumbar spine to a rib cage of a person, the device comprising:

(a) a torso engaging member for at least partially surrounding the torso and for supporting a person proximate a person's waist below the rib cage;

(b) a structure configured to support the torso engaging member;

(c) a seat operatively connected to the device, the seat
(i) an air tight self-inflating chamber constructed from open cell foam;
(ii) a valve for controlling flow of air into and out of the chamber; and
(iii) the chamber having a first height when filled with air and a second, lesser height when air has been removed from the chamber, wherein the torso embracing member supports the person and stress is transferred from the lumbar spine to the rib cage and the stress transferred may be increased by removing air from the chamber;

(d) a cover for the chamber comprising:
(i) a top member having first and second ends;
(ii) a bottom member having first and second ends and operatively connected to said top member to form a cavity therebetween, wherein said chamber is positioned in the cavity; and (e) a first strap having a first end operatively connected to the first end of the bottom member; and (f) a second strap having a first end operatively connected to the second end of the bottom member, second ends of the straps being suitable for connecting to the device; wherein the top member is positioned between the first and second straps and the person to protect the person.

23. The device of claim 22, further comprising said valve extending away from the chamber and proximate the seat's front edge for easy access by the person.

* * * * *

UNITED STATES PATENT AND TRADEMARK OFFICE
CERTIFICATE OF CORRECTION

PATENT NO. : 6,129,693  
DATED : October 10, 2000  
INVENTOR(S) : Peterson

Page 1 of 1

It is certified that error appears in the above-identified patent and that said Letters Patent is hereby corrected as shown below:

<u>Column 5,</u>  
Line 65, "120a" should read -- 120 --

Signed and Sealed this

Thirtieth Day of April, 2002

Attest:

Attesting Officer

JAMES E. ROGAN  
*Director of the United States Patent and Trademark Office*